United States Patent

Bergthaller et al.

[11] Patent Number: 5,908,741
[45] Date of Patent: *Jun. 1, 1999

[54] PHOTOGRAPHIC SILVER HALIDE MATERIAL

[75] Inventors: Peter Bergthaller, Bergisch Gladbach; Hans-Ulrich Borst, Elsdorf; Johannes Willsau, Leverkusen; Ralf Büscher, Lohmar; Peter Bell, Köln, all of Germany

[73] Assignee: Agfa-Gevaert AG, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/701,122

[22] Filed: Aug. 21, 1996

[30] Foreign Application Priority Data

Aug. 31, 1995 [DE] Germany .......................... 195 32 058

[51] Int. Cl.$^6$ ..................................................... G03C 1/09
[52] U.S. Cl. .......................... 430/603; 430/600; 430/607; 430/613
[58] Field of Search .................................... 430/603, 613, 430/607, 600

[56] References Cited

U.S. PATENT DOCUMENTS 5,028,522  7/1991  Kojima et al. .......................... 430/607
5,393,655  2/1995  Sasaki et al. ............................ 430/603
5,567,571  10/1996  Nishikawa ............................... 430/603

FOREIGN PATENT DOCUMENTS 2113346  10/1971  Germany .

*Primary Examiner*—Thorl Chea
*Attorney, Agent, or Firm*—Connolly & Hutz

[57] ABSTRACT

A photographic silver halide material in which the silver halide emulsion layer of at least one silver halide emulsion layer is stabilized with a compound of the formula (I):

$$Ar-Se-X \qquad (I)$$

in which

Ar means a carbocyclic or heterocyclic aromatic group which has an electron-attracting grouping in o-position relative to the Se and X means a further substituted heteroatom, exhibits a smaller reduction in sensitivity, in particular under tropical conditions of storage.

1 Claim, No Drawings

PHOTOGRAPHIC SILVER HALIDE MATERIAL

This invention relates to a photographic silver halide material having at least one silver halide emulsion layer, the silver halide emulsion of which contains a novel stabiliser.

Silver halide emulsions are conventionally protected against changes in their properties by the addition of suitable stabilisers. Stabilisation is in particular required for sensitivity both in the unexposed and exposed state (latent image stability), wherein the most important destabilising influences are temperature and moisture, to which both the unexposed and the exposed but as yet unprocessed silver halide material are constantly subjected.

Known latent image stabilisers such as thiazolidine 4-carboxylic acid of the formula

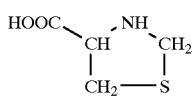

(A)

are insufficiently active, especially under tropical conditions of storage.

The object of the invention was to provide novel stabilisers which protect both the unexposed and exposed silver halide material from any decrease in sensitivity, in particular under tropical conditions of storage.

It has now been found that this object is achieved with certain selenium compounds.

The present invention accordingly provides a photographic silver halide material of the above-stated type, in which at least one silver halide emulsion is stabilised with at least one compound of the formula (I):

$$Ar—Se—X \qquad (I)$$

in which

Ar means a carbocyclic or heterocyclic aromatic group which has an electron-attracting grouping in o-position relative to the Se and X means a further substituted heteroatom, wherein the compound of the formula

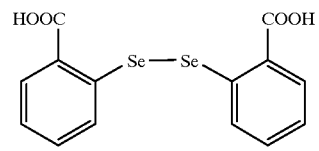

is excepted.

Suitable electron-attracting groups in the o-position of the Ar group are, for example, —CO—Y and —SO$_2$—Y, wherein Y denotes OH, OR$_1$, NH$_2$, NHR$_2$ or NR$_1$R$_2$, wherein R$_1$ means C$_1$–C$_4$ alkyl and R$_2$ means C$_1$–C$_4$ alkyl or phenyl.

Suitable heteroatoms X are, for example, N, P, S and Se, which may be further mono- to trisubstituted, in particular NR$_3$R$_4$, PO(OR$_5$)(OR$_6$), SO$_2$R$_7$, SR$_8$ and SeR$_9$, wherein the following meanings apply:

R$_3$=alkyl, aryl, alkylcarbonyl, arylcarbonyl, dialkylaminocarbonyl, dialkylaminosulphonyl, alkylsulphonyl, arylsulphonyl,
R$_4$=hydrogen or R$_3$, preferably alkyl
R$_5$, R$_6$ mutually independently=hydrogen, alkyl or aryl
R$_7$=alkyl or aryl
R$_8$=alkyl, aryl, a heterocyclic residue, a phosphoric acid ester residue or cyano
R$_9$=alkyl, aryl, in particular a carbocyclic or heterocyclic aromatic group, which has an electron-attracting grouping in o-position relative to the Se.

The alkyl, aryl and heterocyclic residues may be further substituted.

Preferred carbocyclic and heterocyclic aromatic Ar residues are phenyl, thienyl and furyl, which may in particular be further substituted by halogen such as chlorine and bromine, aminocarbonyl, alkoxycarbonyl, aminosulphonyl or carboxy; the amino groups may in turn bear further substituents, in particular phenyl and alkyl groups.

Preferred compounds are symmetrical compounds of the formula (II)

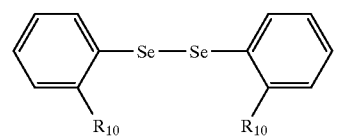

(II)

in which

R$_{10}$ means —COOR$_1$, —CONHR$_2$, —CONH$_2$, —CONR$_1$R$_2$, —SO$_2$NHR$_2$ or —SO$_2$NR$_1$R$_2$ and R$_1$ and R$_2$ have the above-stated meaning.

Typical compounds are:

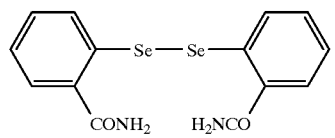

I-1

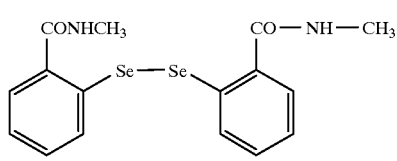

I-2

I-3
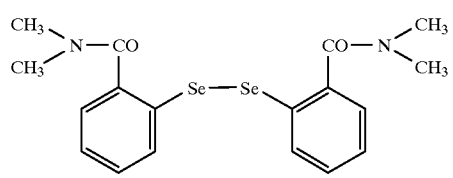
I-4
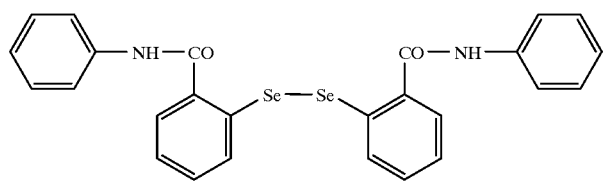
I-5
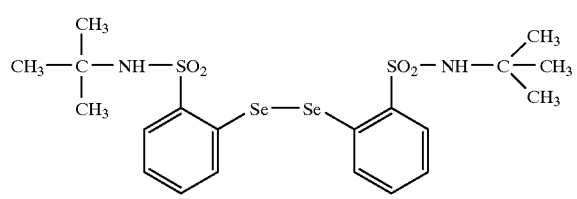
I-6
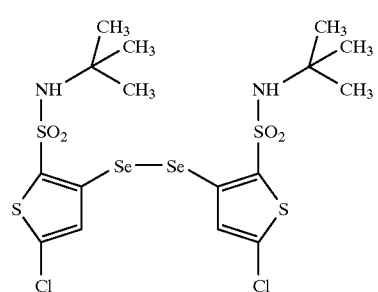
I-7
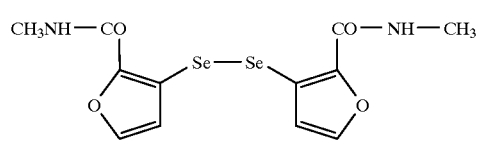
I-8
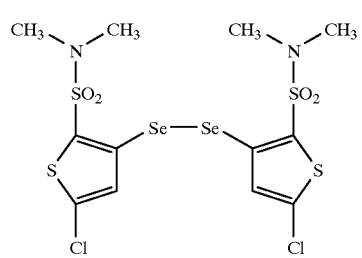
I-9
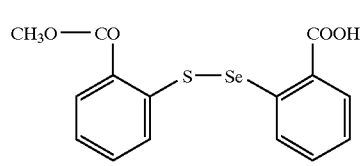

I-10
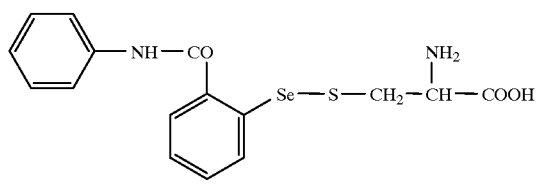
I-11
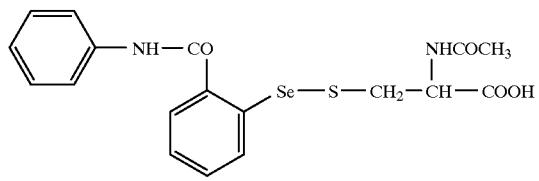
I-12
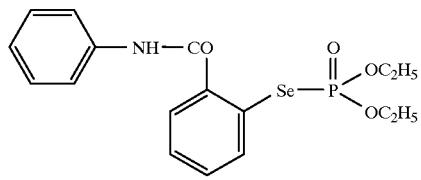
I-13
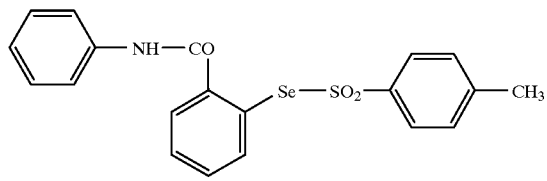
I-14
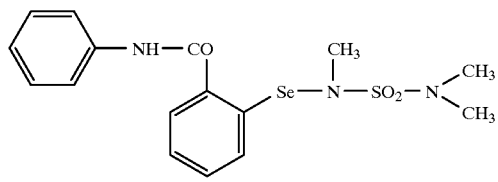
I-15
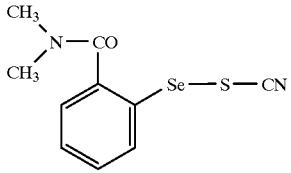
I-16
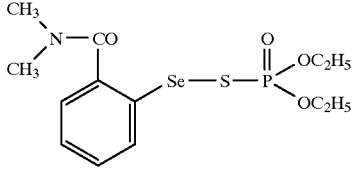

-continued

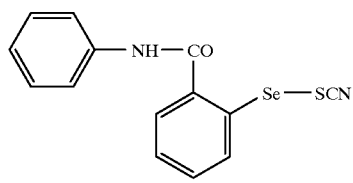

I-17

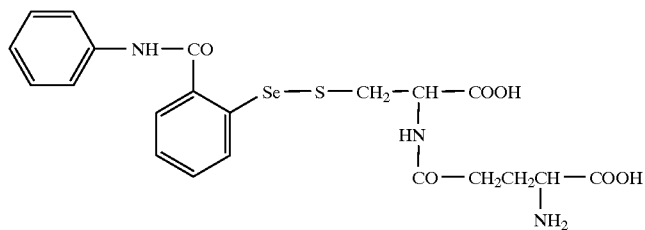

I-18

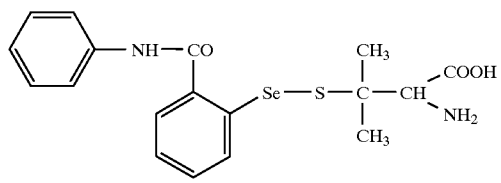

I-19

Production of the compounds is known.

The compounds of the formula (I) are added to the silver halide emulsion to be stabilised in particular in a quantity of $10^{-7}$ to $10^{-3}$ mol/mol of silver halide.

Conventional stabilisaton with amino acids containing sulphur, for example acetylcysteine, or with compound A may additionally provided, wherein these compounds are used in a quantity of $10^{-7}$ to $10^{-3}$ mol/mol of silver halide. The sulphur is here divalent.

Addition is conveniently performed after chemical ripening and spectral sensitisation.

The stabilisers according to the invention are suitable for all photographic silver halide materials, but in particular for colour photographic silver halide materials, preferably for colour negative and colour reversal films having silver halide emulsions which substantially comprise silver bromide-iodide or silver bromide-chloride-iodide emulsion with up to 15 mol. % of silver iodide and up to 30 mol. % of silver chloride, as well as for colour negative and colour reversal papers having silver halide emulsions which contain no iodide and consist to an extent of at least 95 mol. % of AgCl.

Further suitable emulsions are silver chloride emulsions with up to 20 mol. % of AgBr and/or up to 10 mol. % of AgI.

Particularly preferred silver halide emulsions contain tabular grains which constitute at least 50%, preferably 70% of the projected surface area of the emulsion and have an aspect ratio of at least 3:1, in particular of 5:1 to 25:1. Their thickness is preferably less than 0.3 µm, in particular 0.03 to 0.2 µm.

The photographic materials may be developed with conventional colour developer substances, for example N,N-dimethyl-p-phenylenediamine, 4-amino-3-methyl-N-ethyl-N-methoxyethylaniline, 2-amino-5-diethylaminotoluene, N-butyl-N-ω-sulpho-butyl-p-phenylenediamine, 2-amino-5-(N-ethyl-N-β-methanesulphonamidoethylamino)toluene, N-ethyl-N-β-hydroxyethyl-p-phenylenediamine, N,N-bis-(β-hydroxyethyl)-p-phenylenediamine, 2-amino-5-(N-ethyl-N-β-hydroxyethylamino)toluene. Further usable colour developers are described, for example, in *J. Amer. Chem. Soc.* 73, 3100 (1951).

The photographic material may contain conventional colour couplers, which may be incorporated into the silver halide layers themselves. Reference is made to the publications *Farbkuppler* by W. Pelz in *Mitteilungen aus den Forschungslaboratorien der Agfa, Leverkusen/München,* volume III, (1961) and by K. Venkataraman in *The Chemistry of Synthetic Dyes,* vol. 4, 341 to 387, Academic Press, 1971 for examples of usable colour couplers.

Further non-diffusing colour couplers which may be used are 2-equivalent couplers, for example DIR couplers, The non-diffusing colour couplers and chromophoric compounds may be added to the photosensitive silver halide emulsions or other casting solutions using conventional, known methods.

In the event that the non-diffusing colour couplers and chromophoric compounds are compounds which are insoluble in water or alkali, they may be emulsified in a known manner. So-called coupler solvents or oil formers are optionally additionally used for emulsifying such hydrophobic compounds; reference is made, for example, to U.S. Pat. Nos. 2,322,027, 2,533,514, 3,689,271, 3,764,336 and 3,765, 897.

Gelatine is preferably used as the binder for the photographic layers. This may, however, be entirely or partially replaced by other natural or synthetic binders.

The emulsions may also be chemically sensitised, for example by adding compounds containing sulphur during chemical ripening, for example allyl isothiocyanate, allyl thiourea and sodium thiosulphate. Reducing agents may furthermore also be used as chemical sensitisers, for example the tin compounds described in Belgian patents 493 464 or 568 687, together with polyamines such as diethylenetriamine or aminomethylsulphinic acid derivatives, for example according to Belgian patent 547 323, or selenium compounds capable of liberating selenide or selenium, for example selenoureas or heterocyclic selenones, for example the following compounds:

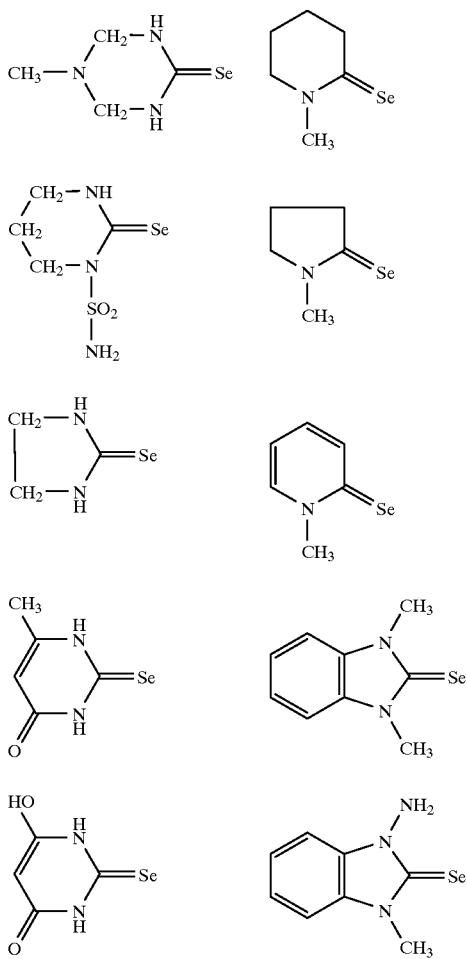

Noble metals or noble metal compounds such as gold, platinum, palladium, iridium, ruthenium or rhodium are also suitable as chemical sensitisers. It is moreover possible to sensitise the emulsions with polyalkylene oxide derivatives, for example with polyethylene oxide of a molecular weight of between 1000 and 20000, and with condensation products of alkylene oxides and alcohols, aliphatic carboxylic acids, aliphatic amines, aliphatic diamines and amides.

The emulsions may also be spectrally sensitised, for example with conventional polymethine dyes, such as neutrocyanines, basic or acidic carbocyanines, rhodacyanines, hemicyanines, styryl dyes, oxonols and the like. Such sensitisers are described in the work by F. M. Hamer *The cyanine dyes and related compounds*, (1964).

The emulsions may contain conventional stabilisers, such as for example homo-polar or salt-like compounds of mercury with aromatic or heterocyclic rings, such as mercapto-triazoles, single mercury salts, sulphonium mercury double salts and other mercury compounds. Also suitable as stabilisers are azaindenes, for example tetra- or penta-azaindenes, in particular those substituted with hydroxyl or amino groups. Such compounds are, for example, described in the article by Birr, *Z. Wiss. Phot.* 47 (1952), 2 to 58. Further suitable stabilisers are, inter alia, heterocyclic mercapto compounds, for example phenylmercaptotetrazole, quaternary benzothiazole derivatives and benzotriazole.

The layers of the photographic material may be hardened in the customary manner, for example with formaldehyde or halogen-substituted aldehydes which contain a carboxyl group, such as mucobromic acid, diketones, methanesulphonic acid esters, dialdehydes and the like. The photographic layers may moreover be hardened with hardeners of the epoxy type, of the heterocyclic ethyleneimine type or of the acryloyl type. It is moreover also possible to harden the layers according to the process of DE-OS 2 218 009 in order to obtain colour photographic materials which are suitable for high temperature processing. It is furthermore possible to harden the photographic layers or the colour photographic multi-layer materials with hardeners of the diazine, triazine or 1,2-dihydroquinoline series. Examples of such hardeners are diazine derivatives containing alkyl or arylsulphonyl groups, derivatives of hydrogenated diazines or triazines, such as for example 1,3,5-hexahydro-triazine, fluorine-substituted diazine derivatives, such as for example fluoropyrimidine, esters of disubstituted 1,2-dihydroquinoline N-carboxylic acids or 1,2-hydroisoquinoline N-carboxylic acids. Also usable are vinylsulphonic acid hardeners, carbodiimide or carbamoyl hardeners, as are, for example, described in DE-OS 2 263 602, DE-OS 2 225 230 and DE-OS 1 808 685, French patent 1 491 807, German patent 872 153 and GDR patent 7218. Further usable hardeners are described, for example, in British patent 1 268 550.

EXAMPLES

Example 1

A non spectrally sensitised silver bromide-iodide emulsion containing 12 mol. % of AgI and substantially consisting of tabular crystals with an average diameter of 1.2 μm and an average aspect ratio of 1:4.5 is ripened to optimum sensitivity with sodium thiosulphate and gold rhodanide and combined with 350 mg of 4-hydroxy-6-methyl-1,3,3a,7-tetraazaindene per 100 g of $AgNO_3$. Six samples are prepared from these emulsions.

Samples 1 and 2 act as a comparison, samples 3 to 6 are according to the invention.

Sample 1 contains $3.2 \times 10^{-6}$ mol of comparison compound A/mol of $AgNO_3$ as stabilising additive Sample 2 contains $3.2 \times 10^{-6}$ mol of diphenyldiselenide 2,2'-dicarboxylic acid/mol of $AgNO_3$ as stabilising additive (comparison compound B according to DE-OS 2,113,346)

| Samples 3 to 6 contain: | Compound |
|---|---|
| 3) $3.2 \times 10^{-6}$ mol/mol of $AgNO_3$ | I-4 |
| 4) $3.2 \times 10^{-6}$ mol/mol of $AgNO_3$ | I-5 |
| 5) $3.2 \times 10^{-6}$ mol/mol of $AgNO_3$ | I-10 |
| 6) $4.8 \times 10^{-6}$ mol/mol of $AgNO_3$ | I-12 |

The samples are cast together with an emulsion of magenta coupler M-1 onto a cellulose triacetate film of a thickness of 120 μm in the following quantities.

Emulsion: 4 g/m² (relative to $AgNO_3$)

Coupler: 68.8 g of emulsion per 100 g of $AgNO_3$

M-1

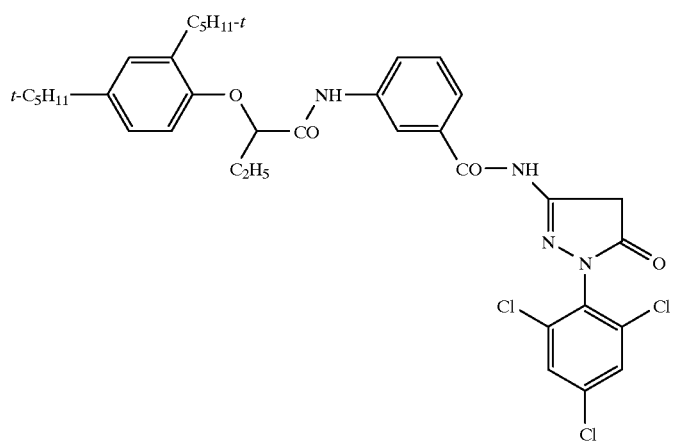

The various materials were exposed behind a graduated step wedge with daylight. The materials were then processed using the process described in *The British J. of Photography* 1974, page 597.

The wedges are stored in both the exposed and unexposed state for 7 days at 20° C. and 45% relative humidity (series A);

for 7 days at 35° C. and 90% relative humidity (series B).

The samples stored unexposed are exposed after storage.

The following sensitivity (E) and fog (S) values are measured through a green filter:

(E in DIN, D in $D_{min}$)

|  |  | Series A | | Series B | |
|---|---|---|---|---|---|
| Sample | | E | S | E | S |
| 1 | exposed | 35.2 | 0.16 | 34.6 | 0.25 |
|  | unexposed | 35.5 | 0.18 | 35.6 | 0.25 |
| 2 | exposed | 34.8 | 0.17 | 34.0 | 0.25 |
|  | unexposed | 35.2 | 0.17 | 33.0 | 0.20 |
| 3 | exposed | 35.3 | 0.15 | 34.5 | 0.20 |
|  | unexposed | 35.5 | 0.15 | 35.8 | 0.20 |
| 4 | exposed | 35.3 | 0.16 | 34.8 | 0.19 |
|  | unexposed | 35.6 | 0.17 | 35.2 | 0.20 |
| 5 | exposed | 35.0 | 0.22 | 34.7 | 0.24 |
|  | unexposed | 35.1 | 0.21 | 35.0 | 0.25 |
| 6 | exposed | 35.1 | 0.20 | 35.0 | 0.25 |
|  | unexposed | 35.3 | 0.20 | 35.0 | 0.22 |

The results show better action in comparison both with known thiazolidine carboxylic acid type stabilisers and with a known diselenide type stabiliser.

Example 2

An AgBrI emulsion (iodide content 2.8 mol. %, median particle size by volume 0.44 μm, distribution range 19%) consisting of above 80%, relative to the projected surface area of the crystals, of hexagonal, tabular crystals (tab grains) with a side length ratio of 1.0–1.5 was chemically ripened at 55° C., pH 6.5 and pAg 7.4 with 3.0 μmol of tetrachloroauric acid, 690 μmol of KSCN and 20 μmol of sodium thiosulphate per mol of Ag (see table). The emulsion was divided between 13 samples which, once chemical ripening was complete, were stabilised as described below (see table).

The samples were cast together with an emulsion of cyan coupler C-1, with 4 mmol of 4-hydroxy-6-methyl-1,3,3a,7-tetraazaindene per mol of Ag and 80 mmol of 1-phenyl-5-mercaptotetrazole per mol of Ag onto a cellulose triacetate film of 120 μm thickness with the following quantities per m².

4.0 g of AgNO₃ (emulsion)

3.0 g of gelatine 0.8 g of cyan coupler C-1

The film samples, hardened with an instant hardener, were stored, exposed and processed as in example 1. The sensitivity data are related to a density of 0.2 above $D_{min}$. Sensitivities are related to the standard emulsion EM-1, which is assigned a value of 100. A halving of the numerical value means a loss of sensitivity of one stop. It may be seen from the table that a considerable improvement in the sensitivity/fog ratio may be achieved with the stabilisers containing selenium according to the invention.

TABLE

| Emul-sion | Addition | Fresh data | | Stored | | Invention |
|---|---|---|---|---|---|---|
|  |  | sensitivity | fog | sensitivity | fog | yes/no |
| Em-1 | — | 100 | 0.32 | 83 | 0.45 | no |
| Em-2/1 | 50 μmol of cmpnd. 1 | 97 | 0.31 | 87 | 0.40 | yes |
| Em-2/2 | 100 μmol of cmpnd. 1 | 97 | 0.33 | 93 | 0.36 | yes |
| Em-3/1 | 50 μmol of cmpnd. 2 | 100 | 0.34 | 93 | 0.38 | yes |
| Em-3/2 | 50 μmol of cmpnd. 3 | 100 | 0.32 | 90 | 0.40 | yes |
| Em-4/1 | 50 μmol of cmpnd. 4 | 93 | 0.30 | 90 | 0.32 | yes |
| Em-4/2 | 100 μmol of cmpnd. 4 | 90 | 0.30 | 87 | 0.33 | yes |
| Em-5/1 | 50 μmol of cmpnd. 5 | 90 | 0.30 | 83 | 0.38 | yes |
| Em-5/2 | 100 μmol of cmpnd. 5 | 87 | 0.31 | 83 | 0.35 | yes |
| Em-6/1 | 50 μmol of cmpnd. 8 | 100 | 0.35 | 97 | 0.37 | yes |
| Em-6/2 | 100 μmol of cmpnd. 8 | 93 | 0.35 | 93 | 0.45 | yes |
| Em-7/1 | 50 μmol of comparison B | 83 | 0.33 | 83 | 0.30 | no |
| Em-7/2 | 100 μmol of comparison B | 83 | 0.32 | 80 | 0.38 | no |

The results show that, when stabilisers containing selenium of the general structure Ar—Se—X according to the invention are used, it is possible to achieve sensitivity advantages, at least over relatively extended storage and on exposure to heat and atmospheric moisture, without its being necessary to accept any increase in fog. Unlike the comparison compound A containing selenium, the selenium compounds according to the invention exhibit stabilising action without a loss of sensitivity.

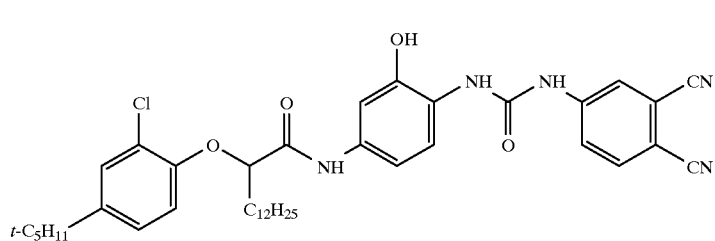

C-1

We claim:

1. Color negative film comprising at least one silver halide emulsion layer, the silver halide emulsion of said silver halide emulsion layer is stabilized with a compound of the formula

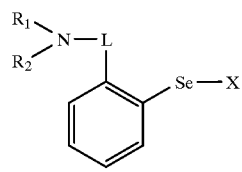

in which

L is —CO— or —SO$_2$— and
X is

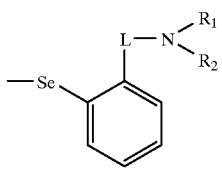

R$_1$ is C$_1$–C$_4$-alkyl
R$_2$ is C$_1$–C$_4$-alkyl or phenyl.

* * * * *